(12) United States Patent
Masury et al.

(10) Patent No.: US 7,201,760 B2
(45) Date of Patent: *Apr. 10, 2007

(54) SURGICAL SCALPEL

(76) Inventors: David H. Masury, 1 Foyes La., Kittery Point, ME (US) 03905; Edward P. Thompson, 57 Salter St., Portsmouth, NH (US) 03801

( * ) Notice: Subject to any disclaimer, the term of this patent is extended or adjusted under 35 U.S.C. 154(b) by 217 days.

This patent is subject to a terminal disclaimer.

(21) Appl. No.: 10/686,302

(22) Filed: Oct. 15, 2003

(65) Prior Publication Data

US 2004/0098002 A1 May 20, 2004

Related U.S. Application Data

(63) Continuation of application No. 10/075,170, filed on Feb. 14, 2002, now Pat. No. 6,645,216.

(51) Int. Cl.
*A61B 17/32* (2006.01)

(52) U.S. Cl. .......................................... 606/167; 30/162

(58) Field of Classification Search ................ 606/167, 606/166, 172; 30/162, 164, 167
See application file for complete search history.

(56) References Cited

U.S. PATENT DOCUMENTS

| | | | |
|---|---|---|---|
| 4,491,132 A * | 1/1985 | Aikins | ......................... 606/170 |
| 4,669,186 A | 6/1987 | Liu | |
| 5,201,748 A | 4/1993 | Newman et al. | |
| 5,258,001 A | 11/1993 | Corman | |
| 5,344,424 A | 9/1994 | Roberts et al. | |
| 5,403,337 A | 4/1995 | Platts | |
| 5,431,672 A | 7/1995 | Cote et al. | |
| 5,475,925 A | 12/1995 | Newman et al. | |
| 5,481,804 A | 1/1996 | Platts | |
| 5,531,754 A | 7/1996 | Shackelford, Sr. et al. | |
| 5,599,351 A | 2/1997 | Haber et al. | |
| 5,626,596 A | 5/1997 | DeSatnick et al. | |
| 5,730,751 A | 3/1998 | Dillon et al. | |
| 5,752,968 A * | 5/1998 | Jolly et al. | ................... 606/167 |
| 5,779,724 A | 7/1998 | Werner | |
| 5,908,432 A | 6/1999 | Pan | |
| 5,919,201 A | 7/1999 | Carter et al. | |

(Continued)

*Primary Examiner*—Michael J. Hayes
*Assistant Examiner*—Nguyen Victor
(74) *Attorney, Agent, or Firm*—Pierce Atwood LLP; Kevin M. Farrell; James M. MacAleenan (57) ABSTRACT

Disclosed is a single-use surgical scalpel having two molded plastic elements, and a surgical blade. The first molded plastic element is a housing. The housing has an upper and a lower radiused edge, and ribbed interior wall surfaces. The ribbed interior wall surfaces of the molded plastic housing define a channel for slidable engagement of the second molded plastic element which is referred to as a blade carrier. The channel has one open end through which a surgical blade is extended during use, a slot through the lower radiused edge for slidable engagement of an actuator/locking fin, a single-use indicator window, and a retaining element for engaging a distal end of a leaf spring. The molded plastic blade carrier has a first end adapted for engaging the surgical blade, a second end having a leaf spring to assist in blade retraction, the leaf spring having a proximal and a distal end, and a central portion having the actuator/locking fin and a single-use indicator. A single-mold embodiment is also disclosed.

19 Claims, 6 Drawing Sheets

U.S. PATENT DOCUMENTS

| | | |
|---|---|---|
| 6,015,419 A | 1/2000 | Strome et al. |
| 6,022,364 A | 2/2000 | Flumene et al. |
| 6,041,505 A | 3/2000 | Chen |
| 6,053,929 A * | 4/2000 | Cohn et al. .................. 606/167 |
| 6,058,607 A * | 5/2000 | Gringer ....................... 30/162 |
| 6,136,013 A | 10/2000 | Marshall et al. |
| 6,254,621 B1 | 7/2001 | Shackelford et al. |
| 6,626,925 B2 * | 9/2003 | Newman et al. ............. 606/167 |
| 6,645,216 B2 * | 11/2003 | Masury et al. .............. 606/167 |

* cited by examiner

SURGICAL SCALPEL

CROSS REFERENCE TO RELATED APPLICATIONS

This application is a Continuation of Application No. 10/075,170, filed Feb. 14, 2002 now U.S. Pat. No. 6,645,216.

BACKGROUND OF THE INVENTION

Surgical scalpels are used by medical personnel in connection with surgical procedures ranging from simple outpatient procedures to extraordinarily complex procedures carried out under general anesthesia. When working with such a sharp instrument, there is always a danger to medical personnel of inadvertent puncture of the skin. Aside from the injury itself, the more important concern for the punctured individual relates to the potential spread of disease from a non-sterile instrument.

The use of surgical scalpels having a retractable blade has been suggested as a means for reducing the number of such puncture wounds. Indeed, a number of patents have been issued which are directed toward surgical scalpels having retractable blades. These include, for example, U.S. Pat. Nos. 5,531,754, 6,254,621, 6,041,505, 6,022,364, 6,015,419, 5,908,432, and 5,779,724. Absent from the disclosure of these referenced U.S. Patents, and any other publication of which Applicant is aware, is a means for determining whether the retractable blade of the surgical scalpel has ever been advanced. In the absence of such an indicator, it may be possible for a previously used scalpel to be mistaken for a new and sterile scalpel. It is certainly less likely that such a mistake could be made if a surgical scalpel equipped with a retractable blade were also designed to incorporate a single-use indicator which would provide a clear indication if the blade of the device were ever extended post-manufacture.

SUMMARY OF THE INVENTION

The present invention relates to a single-use surgical scalpel offering a variety of advantages relative to prior art devices. In preferred embodiments, the surgical scalpel of the present invention consists of three elements: a housing, a blade carrier, and a blade.

The scalpel housing is preferably molded from plastic in an injection molding procedure. As will be seen by reference to the attached drawings, the housing consists of two halves which are either ultrasonically welded together, or held closed by means of snap together features in the assembled device with the blade carrier and blade in place. While the two halves can be molded independently, in preferred embodiments the two halves are molded as a single unit with the two halves being joined by a live hinge.

When assembled, with the two halves ultrasonically welded together, the molded plastic housing has an upper and a lower radiused edge, and interior and exterior wall surfaces. In preferred embodiments, the interior walls of the molded plastic housing are ribbed, with the innermost surfaces of the ribs defining a channel for the slidable engagement of a blade carrier. The use of molded ribs, rather than simply employing an unribbed inner wall surface, offers well known advantages in the injection molding process. In addition, the ribbed bearing surface provides decreased friction in blade carrier movement when compared to the frictional forces encountered with a non-ribbed bearing surface. Other features of the channel include, an open end through which a surgical blade is extended during use, a slot through the lower radiused edge for slidable engagement of an actuator/locking fin, a single-use indicator window, and a retaining element for engaging a distal end of a leaf spring.

The molded plastic blade carrier, which is slidably engaged by the channel defined by the ribbed interior wall surface of the housing, includes a first end adapted for engaging the surgical blade, and a second end comprising a leaf spring to assist in blade retraction, the leaf spring having a proximal and a distal end. The blade carrier also includes a central portion which includes the actuator/locking fin and a single-use indicator.

DESCRIPTION OF PREFERRED EMBODIMENTS

Figure 1:
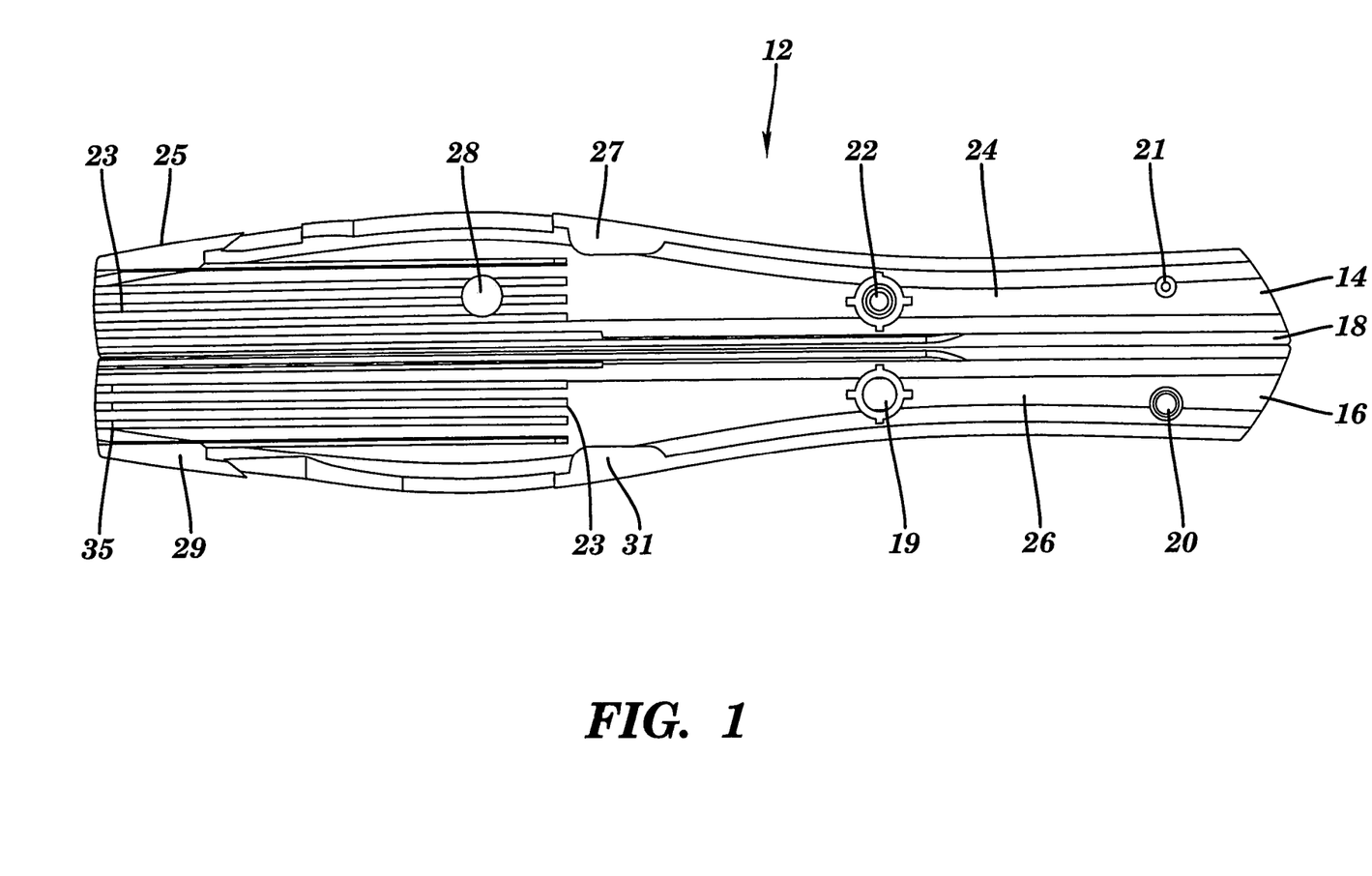
FIG. 1 is a plan view of the housing of the device of the present invention, in unassembled form.

Referring to FIG. 1, an element of the device of the present invention is shown in plan view. More specifically, FIG. 1 depicts a molded plastic housing (12). The housing consists of a first half (14), and a second half (16), which are mated in the assembled device. While the first half (14) and the second half (16) can be independently molded prior to assembly, in preferred embodiments, the two halves are molded as a single unit and joined by a live hinge (18) which runs longitudinally and defines a common edge of each half. The live hinge (18) is essentially a thinly molded plastic strip which holds the two halves together and, by virtue of its thinness, enables the two halves to mate without breaking the hinge. Also shown in FIG. 1 is a molded press fit with male (21) and female (20) elements designed to hold the mated halves (14 and 16) together in the assembled device prior to ultrasonic welding. Ultrasonic welding flanges (25, 27, 29 and 31) are provided to effectively and permanently weld halves 14 and 16 together following assembly. Alternatively, permanent type snap together features (not illustrated) may be used in place of the ultrasonic welding to assemble the halves 14 and 16.

The interior walls (24 and 26) of halves 14 and 16 carry molded ribs (23) which define a channel for slidable engagement of a blade carrier. As discussed briefly above, the use of a ribbed bearing surface, as opposed to unribbed interior wall surfaces, offers advantages in the injection molding process. The ribs create a thicker and stiffer wall section whole reducing the volume of the material (relative to a solid wall of equal thickness). The reduction in thick sections prevents sink marks from occurring on the outer surfaces of the handle. These sink marks are caused by the shrinkage of the plastic during the cooling portion of the molding cycle. In addition, ribbed bearing surfaces offer less frictional resistance to a moving blade carrier than would unribbed interior wall surfaces.

Item 22 is a molded retaining element designed to anchor the distal end of a leaf spring element of the blade carrier. Item 22 is dimensioned for a secure press fit in molded receiving element (19). In preferred embodiments, the retaining element is an anchoring boss which engages a ring on the distal end of the leaf spring. Item 28 is a viewing window to provide for visual inspection of a single-use indicator.

Figure 2:
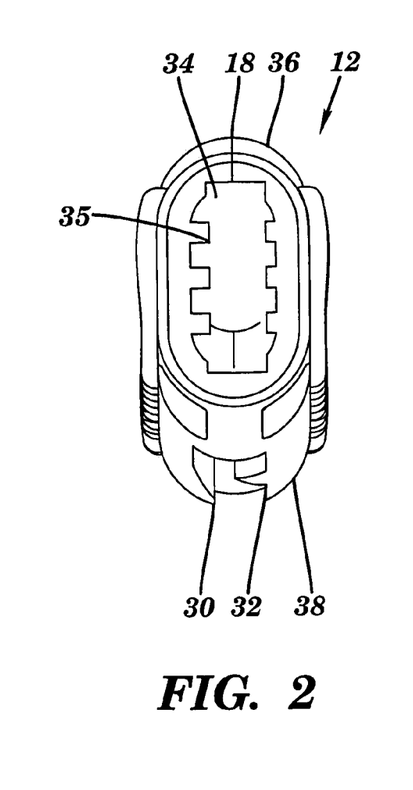
FIG. 2 is a front end view of the housing of the device of the present invention, in assembled form.
Figure 3:
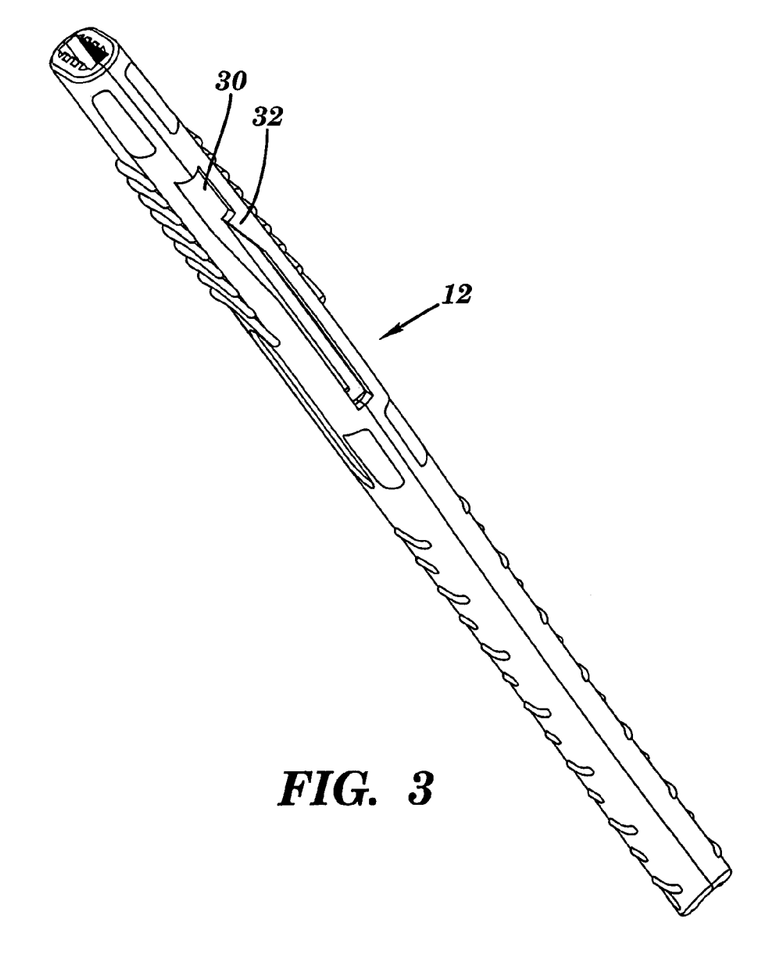
FIG. 3 is a bottom isometric view of the housing of the device of the present invention showing two-mated halves with blade carrier and blade omitted.

FIGS. 2 and 3 are, respectively, an end plan view and a bottom isometric view of the assembled housing in which no blade carrier or blade has been inserted. These drawings are included to provide views of specific elements of the housing which are not clearly seen in the unassembled housing halves of FIG. 1. Viewing end-on, FIG. 2 shows one end of the assembled housing contains an opening (34) in communication with the interior channel of the housing (12). Reference numeral 35 is directed toward a shimming end of a rib. Shimming ends (35) will be discussed in more detail in connection with FIGS. 5 and 6. FIG. 2 also shows that the top edge (36) and the bottom edge (38) of the housing (12) are radiused for comfort and control.

Referring to FIG. 3, a scalpel of the present invention is shown isometrically, from below. Depicted is a live hinge (18), joining housing halves 14 and 16. The lower edge of the assembled housing (12) contains a slot (30) for slidable engagement of an actuator/locking fin, which is an element of the blade carrier. In preferred embodiments, a molded ramp (32) extends from one edge of the wall which defines the slot (30). The molded ramp (32) functions to retain the blade carrier in a blade-extended position during use.

Figure 4:
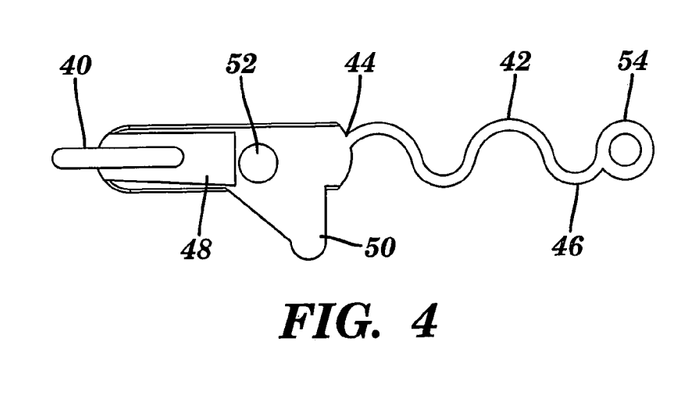
FIG. 4 is a right side plan view of the blade carrier of the present invention.

Referring to FIG. 4, the blade carrier of the present invention is shown in a right side plan view. The blade carrier can be seen generally as consisting of three portions: a first end comprising a surgical blade engagement mold (40), a second end comprising a leaf spring (42) to assist in blade retraction, the leaf spring having a proximal (44) and a distal end (46), and a central portion (48) comprising an actuator/locking fin (50) and a single-use indicator (52). One of the many advantages of the present invention is that the blade carrier can be molded as a single unit from plastic. The use of a leaf spring, rather than a metal coil spring, enables this advance over the art. Also shown in FIG. 4 is a molded anchoring ring (54) which engages the anchoring boss depicted in, and discussed in connection with, FIG. 1.

Figure 5:
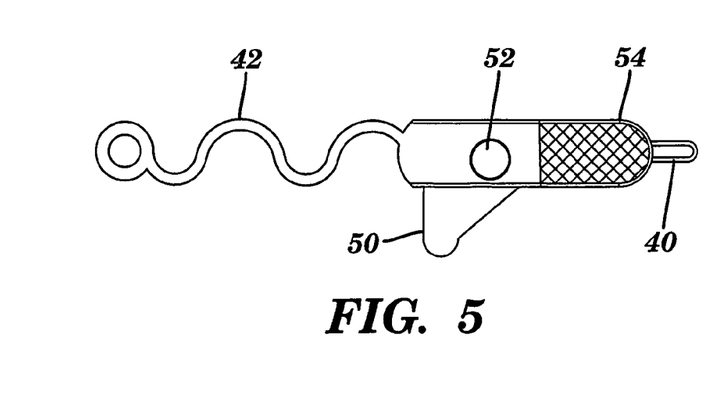
FIG. 5 is a left side plan view of the blade carrier of the present invention.

FIG. 5 is a left side plan view of the blade carrier of the present invention. The left side plan view shows features, or portions of features depicted in FIG. 4, including: surgical blade engagement mold (40), leaf spring (42), locking/actuator fin (50), and single use indicator (52). In addition, FIG. 5 shows a shimming plane (54). Shimming plane (54) is tapered and serves to increase the overall thickness of the blade carrier from the blade engagement mold, rearward. In use, as the blade is extended using the locking/actuator fin, the shimming plane (54) makes contact with a shimming end of a rib (see reference numeral 35 in FIG. 3). Ribs (23) as shown in FIG. 1, are tapered near opening 34. The taper of the rib complements the taper of the shimming surface (54) of the blade carrier edge thereby eliminating any unwanted blade movement when the blade carrier is locked in the blade-extended position. Initial contact between shimming plane (54) and a rib shimming end is made early in the travel of the blade carrier from the blade-withdrawn to the blade-extended position. The increase in thickness from the blade engagement mold, rearward, is calibrated such that the blade engagement mold portion is securely shimmed in the blade-extended position.

Figure 6:
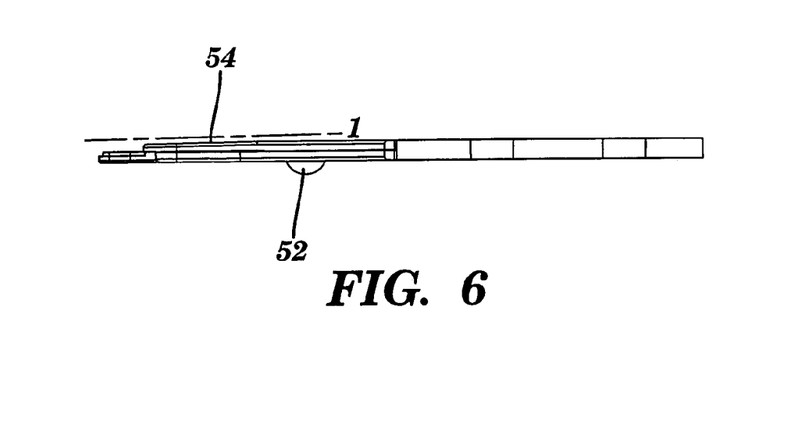
FIG. 6 is a top view of the blade carrier of the present invention.

Line 1—1 of FIG. 6 is intended to provide a sense of the slope of shimming plane 54. One of skill in the art will recognize that the slope of an effecting shimming plane could vary dramatically depending upon the tolerances provided at the open end through which the blade extends. FIG. 6 also provides a profile view of a preferred embodiment of the single-use indicator (52). The single-use indicator is shown as a thinly molded convex bubble of plastic, the concave side of which is seen in FIG. 5.

Figures 7, 8:
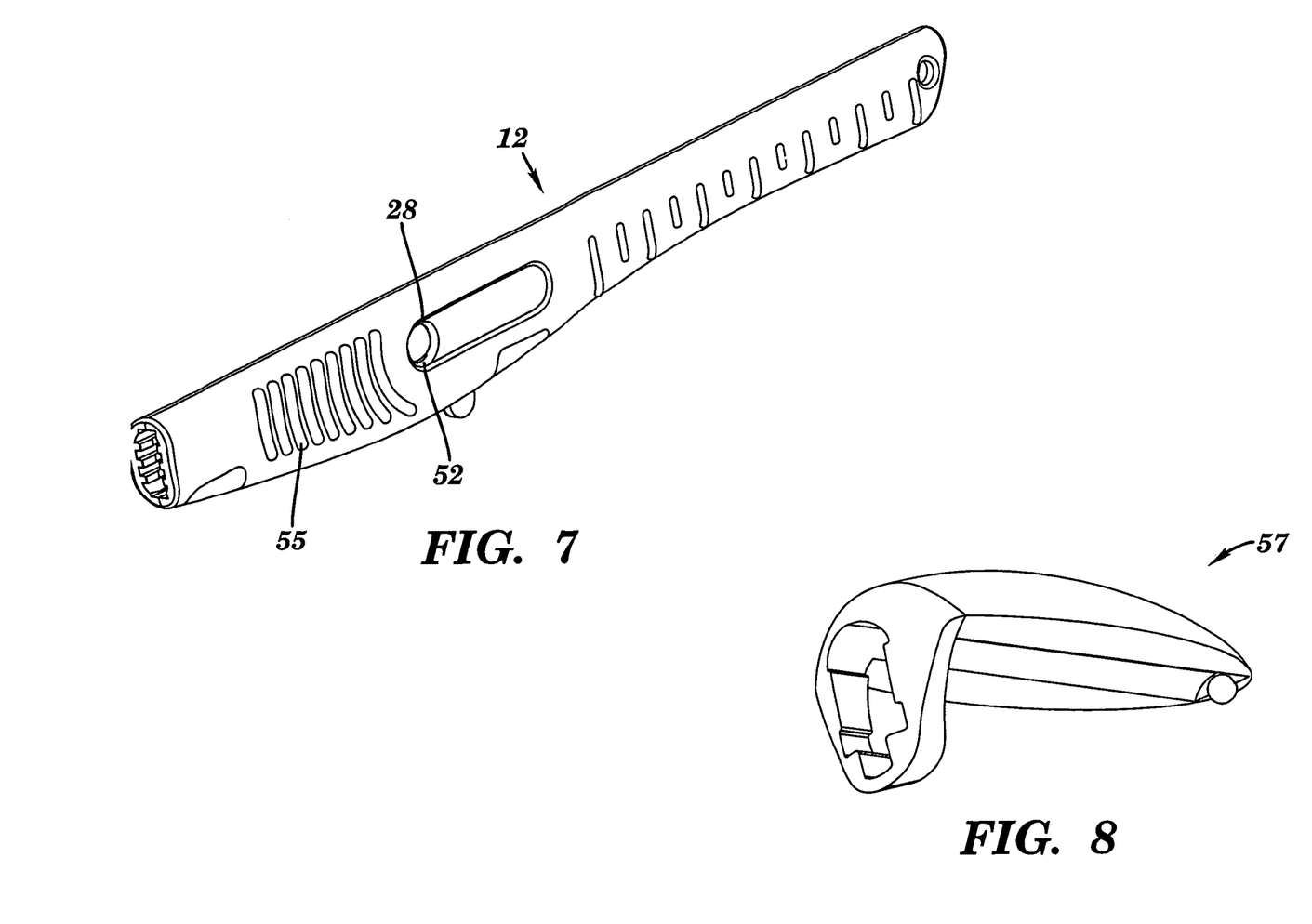
FIG. 7 is an isometric view of the fully assembled device in the blade-retracted position.
FIG. 8 is an isometric bottom view of an optional palm-support attachment.

Referring to FIG. 7, with the surgical blade in the fully retracted position, single-use indicator 52 occupies viewing window 28, within housing 12. As the locking/actuator fin (50) is advanced to extend the surgical blade, the single use indicator (52) is irreversibly collapsed or inverted by contact with the ribbed interior wall surface. In preferred embodiments, the ribs making initial contact with the single-use indicator bubble are ramped. Ramping tends to minimize the possibility that any portion of the single-use indicator bubble (52) could be broken loose within the housing as the blade carrier is advanced. Such an occurrence would be much more likely if the bubble encountered a squared rib edge while the blade carrier was advanced.

When the surgical blade is subsequently retracted, visual observation through viewing window (28) will clearly indicate that the surgical blade has been previously extended. In the clinical setting, observation that the surgical blade has been previously extended would dictate disposal of the device. FIG. 7 also shows molded fins (55) on the housing (12) in critical gripping locations.

Figure 9:
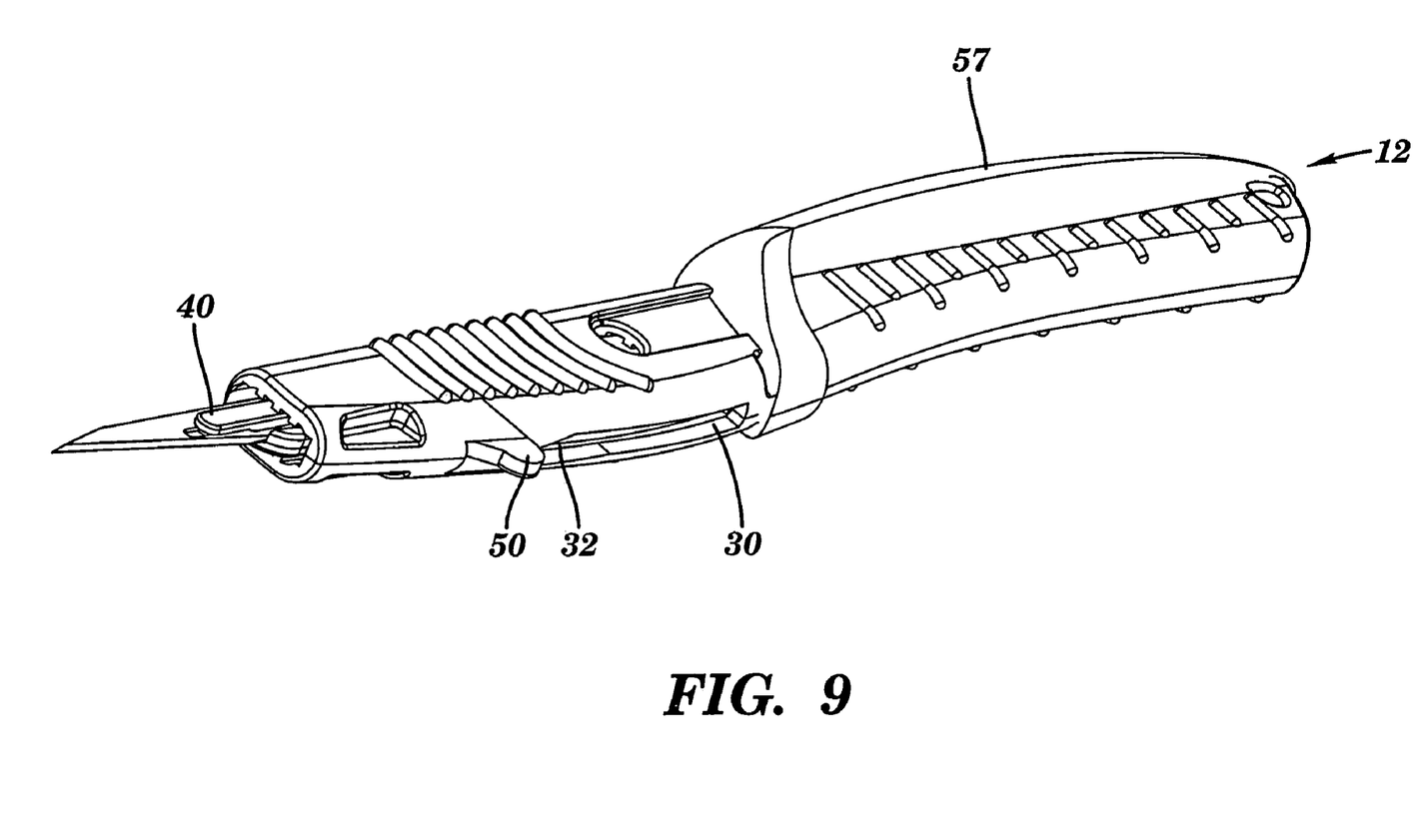
FIG. 9 is an isometric bottom view of the optional palm-support attachment positioned on the scalpel of the present invention with surgical blade extended.

For overhand use, primarily in connection with gross-cutting activities, the device of the present invention can be fitted with an optional palm-support (57) enabling increased control in an overhand cutting mode. The optional support attaches, for example, by friction fit or snap fit. It will be recognized that the palm support could be molded together with the housing making it an integral (i.e. non-optional) palm support. An isometric bottom view of this optional attachment is shown in FIG. 8, and FIG. 9 shows an isometric bottom view of the optional device attached to an assembled scalpel in the blade-extended position.

The surgical scalpel of the present invention can also be fitted with an optional high intensity lighting system. The lighting system, not shown in the drawings, comprises a battery, bulb and fiber optic strand. Molded within the housing (12), preferably rearward of the channel for the blade carrier, would be a molded cavity for receiving the batter and high intensity bulb. A fiber optic strand, preferably acrylic, would be positioned adjacent the live hinge. During the molding process, an appropriately dimensioned channel could be formed for accepting a fiber optic strand. The fiber optic strand would carry light to the working end of the scalpel. An optional lens could be positioned near the terminus of the fiber optic strand to provide adjustable focus of the emitted light beam.

The high intensity bulb is typically provided with two contact legs. In a preferred embodiment, one contact leg is permanently contacted with a battery. The lighting circuit is completed when the second leg of the bulb is contacted with the battery. In preferred embodiments, movement of actuator/locking fin (50) forward into the blade-extended mode would drive the second leg into battery contact, thereby completing the lighting circuit.

Figure 10:
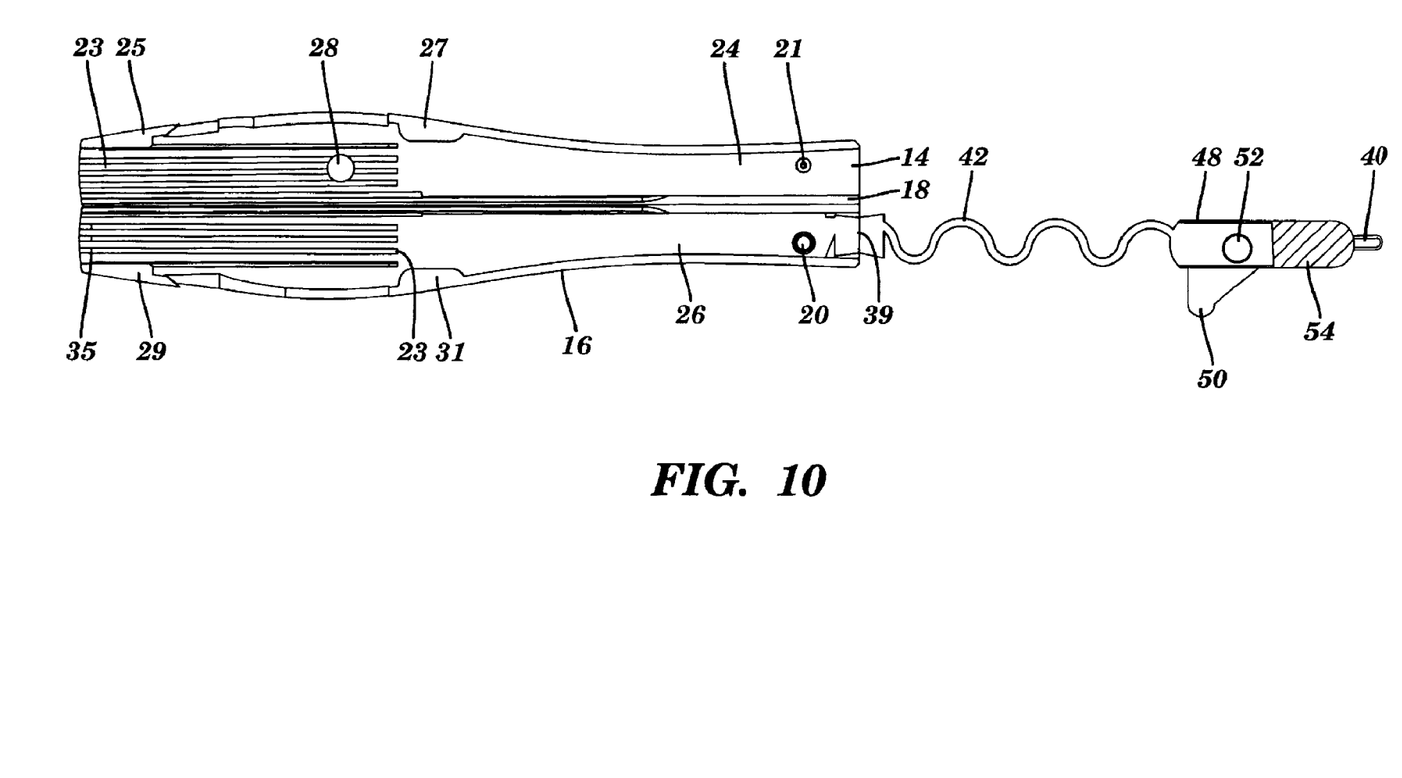
FIG. 10 is a plan view of a single-mold embodiment of the present invention.

Referring to FIG. 10, a single-mold embodiment of the present invention is represented. Elements common to this embodiment, and those previously described include, housing halves (14 & 16); live hinge (18); molded press fit with male (21) and female (20) elements; inner wall surface ribs (23); interior wall surfaces (24 and 26); ultrasonic welding flanges (25, 27, 29 and 31); viewing window (28); rib shimming end (35); surgical blade engagement mold (40); leaf spring (42); locking/actuator fin (50); single use indicator (52); shimming plane (54); and central portion (48) of the blade carrier. A unique aspect to this embodiment is a second live hinge (39) which joins the blade carrier assembly to the housing.

The invention claimed is:

1. A surgical scalpel comprising:
   a housing having an internal channel and a viewing window formed therein; and
   a blade carrier slidably disposed in said channel for movement between a retracted position and an extended position, said blade carrier including a single use indicator that is visible through said viewing window when said blade carrier is in said retracted position and is structurally altered when said blade carrier is moved to said extended position wherein said blade carrier includes an actuator/locking fin that, when advanced, simultaneously advances a surgical blade, resulting in the single use indicator that is one of irreversibly collapsed and inverted by contact with a plurality of ribbed interior wall surfaces.

2. The surgical scalpel of claim 1 wherein said single use indicator is a flexible convex element that is irreversibly collapsed when said blade carrier is moved to said extended position.

3. The surgical scalpel of claim 1 wherein a portion of said blade carrier is tapered to form a shimming plane that contacts an interior wall surface of said internal channel when said blade carrier is in said extended position.

4. The surgical scalpel of claim 3 further comprising one or more tapered ribs formed on said interior wall surface.

5. The surgical scalpel of claim 1 wherein said housing includes a slot formed therein and said blade carrier includes an actuator/locking fin that extends through said slot.

6. The surgical scalpel of claim 5 wherein said slot includes a ramp formed therein for engaging said actuator/locking fin when said blade carrier is in said extended position.

7. The surgical scalpel of claim 1 wherein said blade carrier includes a leaf spring extending outwardly therefrom, said leaf spring having a distal end that engages said housing.

8. The surgical scalpel of claim 1 further comprising a palm support removably attached to said housing.

9. The surgical scalpel of claim 1 further comprising a plurality of raised ribs formed on an exterior surface of said housing.

10. The surgical scalpel of claim 1 wherein said housing is a molded plastic housing of unitary construct.

11. A surgical scalpel comprising:
    a housing having an internal channel and a viewing window formed therein;
    a blade carrier slidably disposed in said channel for movement between a retracted position and an extended position, said blade carrier having a first end adapted to engage a surgical blade and a leaf spring extending from a second end thereof, said leaf spring having a distal end that engages said housing, said blade carrier further including a single use indicator that is visible through said viewing window when said blade carrier is in said retracted position and is structurally altered when said blade carrier is moved to said extended position wherein said blade carrier includes an actuator/locking fin that, when advanced, simultaneously advances the surgical blade, resulting in the single use indicator that is one of irreversibly collapsed and inverted by contact with a plurality of ribbed interior wall surfaces; and
    a surgical blade attached to said first end of said blade carrier.

12. The surgical scalpel of claim 11 wherein said single use indicator is a flexible convex element that is irreversibly collapsed when said blade carrier is moved to said extended position.

13. The surgical scalpel of claim 11 wherein a portion of said blade carrier is tapered to form a shimming plane that contacts an interior wall surface of said internal channel when said blade carrier is in said extended position.

14. The surgical scalpel of claim 13 further comprising one or more tapered ribs formed on said interior wall surface.

15. The surgical scalpel of claim 11 wherein said housing includes a slot formed therein and said blade carrier includes an actuator/locking fin that extends through said slot.

16. The surgical scalpel of claim 11 wherein said slot includes a ramp formed therein for engaging said actuator/locking fin when said blade carrier is in said extended position.

17. The surgical scalpel of claim 11 further comprising a palm support removably attached to said housing.

18. The surgical scalpel of claim 11 further comprising a plurality of raised ribs formed on an exterior surface of said housing.

19. The surgical scalpel of claim 11 wherein said housing is a molded plastic housing of unitary construct.

* * * * *

UNITED STATES PATENT AND TRADEMARK OFFICE
CERTIFICATE OF CORRECTION

| | | |
|---|---|---|
| PATENT NO. | : 7,201,760 B2 | |
| APPLICATION NO. | : 10/686302 | |
| DATED | : April 10, 2007 | |
| INVENTOR(S) | : David H. Masury | |

It is certified that error appears in the above-identified patent and that said Letters Patent is hereby corrected as shown below:

Col. 6, claim 16, line 43, delete "claim 11" and substitute --claim 15--.

Signed and Sealed this

Nineteenth Day of June, 2007

JON W. DUDAS
*Director of the United States Patent and Trademark Office*